(12) United States Patent
Grajcar

(10) Patent No.: US 11,376,340 B2
(45) Date of Patent: Jul. 5, 2022

(54) BIOSECURITY SYSTEM USING MONITORING AND SANITIZATION FOR AN AGRICULTURAL DWELLING

(71) Applicant: SIGNIFY NORTH AMERICA CORPORATION, Somerset, NJ (US)

(72) Inventor: Zdenko Grajcar, Orono, MN (US)

(73) Assignee: SIGNIFY NORTH AMERICA CORPORATION, Somerset, NJ (US)

( * ) Notice: Subject to any disclaimer, the term of this patent is extended or adjusted under 35 U.S.C. 154(b) by 63 days.

(21) Appl. No.: 16/072,230

(22) PCT Filed: Jan. 24, 2017

(86) PCT No.: PCT/US2017/014743
§ 371 (c)(1),
(2) Date: Jul. 24, 2018

(87) PCT Pub. No.: WO2017/132146
PCT Pub. Date: Aug. 3, 2017

(65) Prior Publication Data
US 2019/0269809 A1     Sep. 5, 2019

Related U.S. Application Data

(60) Provisional application No. 62/286,487, filed on Jan. 25, 2016.

(51) Int. Cl.
*A61L 2/10* (2006.01)
*A61L 9/20* (2006.01)
(Continued)

(52) U.S. Cl.
CPC ..................... *A61L 2/10* (2013.01);
*A23L 3/26* (2013.01); *A23L 3/28* (2013.01);
*A61L 2/202* (2013.01);
(Continued)

(58) Field of Classification Search
None
See application file for complete search history.

(56) References Cited

U.S. PATENT DOCUMENTS 6,254,625 B1   7/2001   Rosenthal et al.
8,754,385 B1   6/2014   Gutman
(Continued)

FOREIGN PATENT DOCUMENTS

KR        101263488 B1      6/2013
KR     20130004276 U  *    7/2013
(Continued)

OTHER PUBLICATIONS

Adams, "Keeping Chickens and Rabbits in the Greenhouse" Garden & Greenhouse (Oct. 2013) (archive.org capture from Aug. 8, 2015) (Year: 2013).*

(Continued)

*Primary Examiner* — James Choi

(57) ABSTRACT

Sanitizing an agricultural facility by placing a chamber having an open interior within the agricultural facility. An item is placed within an open interior of the chamber and a door is interlocked. Then light having a spectral content within a narrow range of wavelengths is provided from at least one lighting device toward the item for a predetermined amount of time to inactivate a microorganism. Simultaneously, ozone may be discharged into the open interior to sanitize the item. Before the door unlocks the ozone within the interior of the chamber is directed to a filter for forming oxygen. Sanitizing the agricultural facility by detect humans, and in response, providing a first light with one spectral content when the human is detected, and providing a second light with a different spectral content within a narrow range of wavelengths to inhibit bacteria growth when humans are not detected.

16 Claims, 10 Drawing Sheets

(51) Int. Cl.
*A23L 3/28* (2006.01)
*A61L 2/20* (2006.01)
*A61L 2/24* (2006.01)
*A61L 9/015* (2006.01)
*A23L 3/26* (2006.01)
*A23L 3/3418* (2006.01)
*A61N 5/06* (2006.01)

(52) U.S. Cl.
CPC ............... *A61L 2/24* (2013.01); *A61L 9/015* (2013.01); *A23L 3/3418* (2013.01); *A61L 9/20* (2013.01); *A61L 2202/11* (2013.01); *A61L 2202/122* (2013.01); *A61L 2202/13* (2013.01); *A61L 2202/14* (2013.01); *A61L 2202/25* (2013.01); *A61L 2209/111* (2013.01); *A61L 2209/212* (2013.01); *A61N 5/0624* (2013.01); *A61N 2005/0661* (2013.01); *A61N 2005/0662* (2013.01)

(56) References Cited

U.S. PATENT DOCUMENTS

| | | | |
|---|---|---|---|
| 2003/0059505 A1 | 3/2003 | Yousef et al. | |
| 2005/0167349 A1 | 8/2005 | Holler | |
| 2005/0186108 A1 | 8/2005 | Fields | |
| 2005/0276720 A1 | 12/2005 | Correa | |
| 2006/0140817 A1 | 6/2006 | Cumberland et al. | |
| 2007/0172560 A1 | 7/2007 | Mirtsching et al. | |
| 2008/0298052 A1* | 12/2008 | Hurst | A01G 7/045 362/231 |
| 2009/0280223 A1 | 11/2009 | Scott | |
| 2010/0266445 A1 | 10/2010 | Campagna | |
| 2010/0266716 A1 | 10/2010 | Olson et al. | |
| 2011/0163246 A1* | 7/2011 | Ishiwata | A01G 7/045 250/492.1 |
| 2012/0261590 A1 | 10/2012 | Boyle | |
| 2014/0060104 A1* | 3/2014 | Shur | A61L 2/10 62/264 |
| 2014/0105930 A1 | 4/2014 | Springer | |
| 2014/0264074 A1 | 9/2014 | Victor et al. | |
| 2015/0062893 A1* | 3/2015 | Lynn | A61L 2/10 362/231 |
| 2015/0343103 A1 | 12/2015 | Grajcar et al. | |
| 2016/0183499 A1 | 6/2016 | Grajcar | |
| 2018/0054974 A1* | 3/2018 | Vasilenko | H05B 45/10 |

FOREIGN PATENT DOCUMENTS

| | | |
|---|---|---|
| RU | 2431418 C1 | 10/2011 |
| WO | 03078571 A2 | 9/2003 |
| WO | WO-2015130786 A1 | 9/2015 |
| WO | WO-2016081594 A1 | 5/2016 |
| WO | WO-2017132146 A1 | 8/2017 |

OTHER PUBLICATIONS

Yin et al., Light based anti-infectives: ultraviolet C irradiation, photodynamic therapy, blue light, and beyond, Current Opinion in Pharmacology 2013, 13:731-762 (Year: 2013).*

"International Application Serial No. PCT/US2017/014743, International Preliminary Report on Patentability dated Aug. 9, 2018", 6 pgs.

"International Application Serial No. PCT/US2018/067265, International Search Report dated Apr. 23, 2019", 4 pgs.

"International Application Serial No. PCT/US2018/067265, Written Opinion dated Apr. 23, 2019", 10 pgs.

"U.S. Appl. No. 14/728,261, Amendment and Response filed Jan. 28, 2016 to Non-Final Office Action dated Aug. 28, 2015", 7 pgs.

"U.S. Appl. No. 14/728,261, Appeal Brief filed Feb. 3, 2017", 15 pgs.

"U.S. Appl. No. 14/728,261, Final Office Action dated May 2, 2016", 10 pgs.

"U.S. Appl. No. 14/728,261, Non Final Office Action dated Aug. 28, 2015", 11 pgs.

"International Application Serial No. PCT/US2017/014743, International Search Report dated Apr. 6, 2017", 2 pgs.

"International Application Serial No. PCT/US2017/014743, Written Opinion dated Apr. 6, 2017", 4 pgs.

Schoborg, et al., "Porcine epidemic diarrhea virus (PEDV) co-infection induced chlamydial persistence/stress does not require viral replication", Frontiers in Cellular and Infection Microbiology, vol. 4, article 20, (Mar. 13, 2014), 1-10.

Zhang, Howard Q, et al., "Nonthermal processing of food", Blackwell Publishing, (2011), 254.

* cited by examiner

BIOSECURITY SYSTEM USING MONITORING AND SANITIZATION FOR AN AGRICULTURAL DWELLING

CLAIM OF PRIORITY

This patent application is a U.S. National Stage Filing under 35 U.S.C. 371 from International Patent Application Serial No. PCT/US2017/014743, filed. Jan. 24, 2017, published on Aug. 3, 2017 as WO 2017/132146 A1, which application claims the benefit of priority of U.S. Provisional Patent Application Ser. No. 62/286,487, entitled "Biosecurity System for Agricultural Dwelling," filed on Jan. 25, 2016, each of which are hereby incorporated by reference herein in their entireties.

TECHNICAL FIELD

This patent application is directed generally, but not by way of limitation, to biosecurity. More specifically, toward a biosecurity system for an agricultural dwelling.

BACKGROUND

Over the last several decades the agricultural industry has gone from traditional family farms that typically are outdoors to large corporate farms and processing plants that are mainly indoors. While such a move was done to increase efficiencies and reduce costs, new found problems have occurred. In particular, over the last several years virus and bacteria have infiltrated agricultural facilities. In the swine industry the Porcine Epidemic Diarrhea (PED) virus has wiped out entire swine farms in North America. Meanwhile poultry have been hit with the avian flu on multiple occasions over the last several years.

When these diseases infiltrate a farm, whether swine or poultry, typically all of the animals must be culled and the building completely scrubbed down and sanitized to get rid of the disease. This process causes a complete loss of the flock or litters, costing farms millions of dollars in damages from lost livestock. In addition, the entire industry is effected when growers are unable to keep up with supply demands during such a time, thereby raising costs and harming the industry.

As a result, agricultural building typically have protocols in place regarding visitors and those working in such a facility. For instance, often those that have visited another corporate farm in a previous month are not allowed onto a different farm. Also coverings at facilities are provided for individual's feet to stop potential bacteria or virus on shoes from being tracked into a facility.

Other methods have been developed to reduce virus and bacteria within agricultural facilities. For example, biosecure chambers exist in the art that utilize UV light within the chamber so that clothing and items such as keys, wallets, food containers and the like can be placed in the chamber for a predetermined period of time to inactivate or kill all bacteria and viruses on the surfaces the receive the UV light. Alternatively, by eliminating red light within a lighting fixture that promotes bacteria growth, and using blue light that inhibits bacteria growth, lighting devices can be provided that increase biosecurity and reduce bacteria.

Still, problems remain. In particular, while utilizing blue light can have positive effects on poultry or livestock, humans typically prefer the use of white light in working environments. Therefore blue lighting is not utilized within agricultural facilities and viruses and bacteria remain problematic. Thus, a need in the art exists for an improved biosecurity system for an agricultural dwelling.

SUMMARY

A method of sanitizing an agricultural facility, including monitoring at least one room of an agricultural facility with a sensor to detect a human. A first light having a first spectral content is provided when a human is detected. Then when a human is no longer detected a second light having a second spectral content within a narrow range of wavelengths to inhibit bacteria growth is provided.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
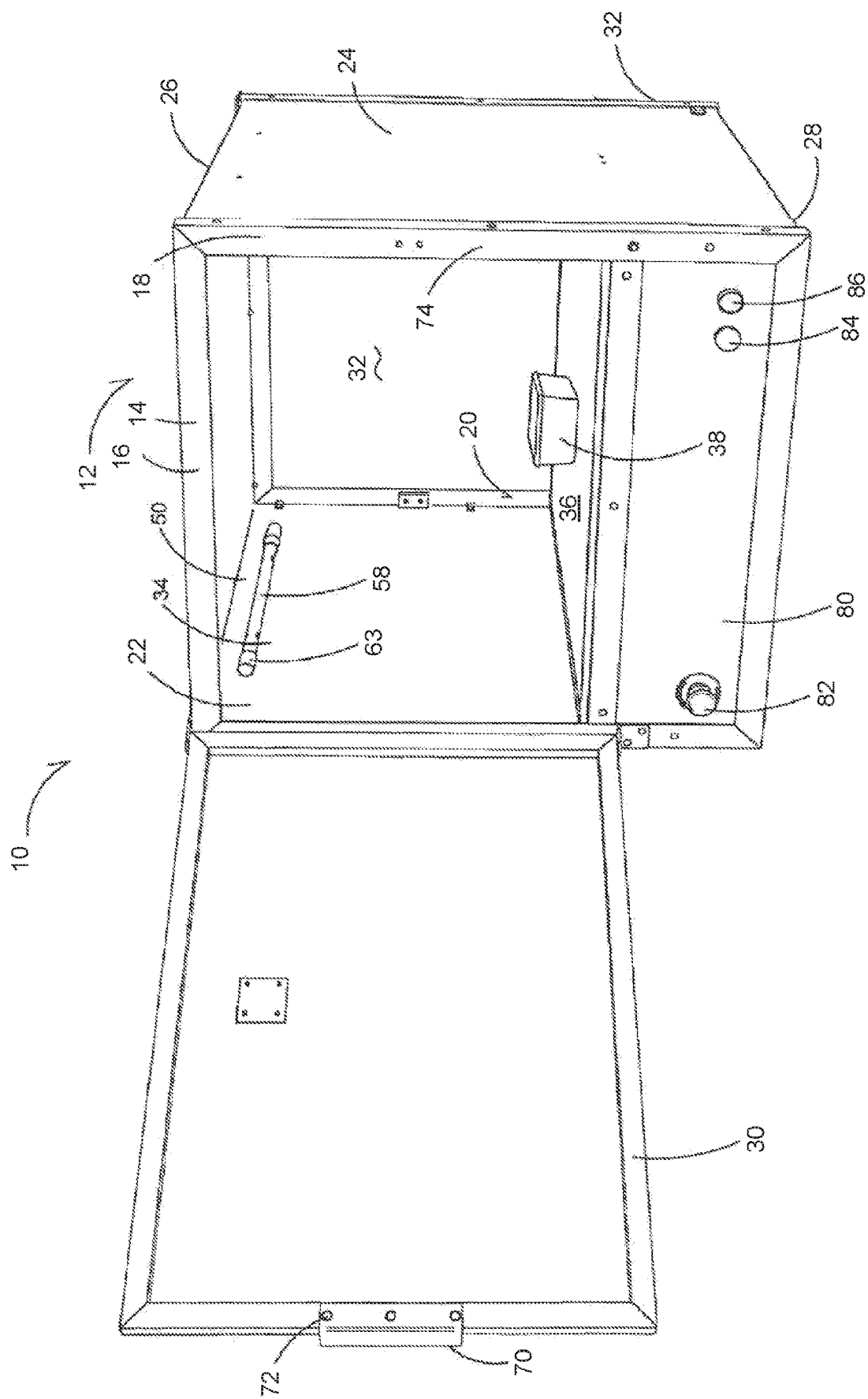
FIG. 1 is a perspective view of a sanitation chamber in an open position.
Figure 2:
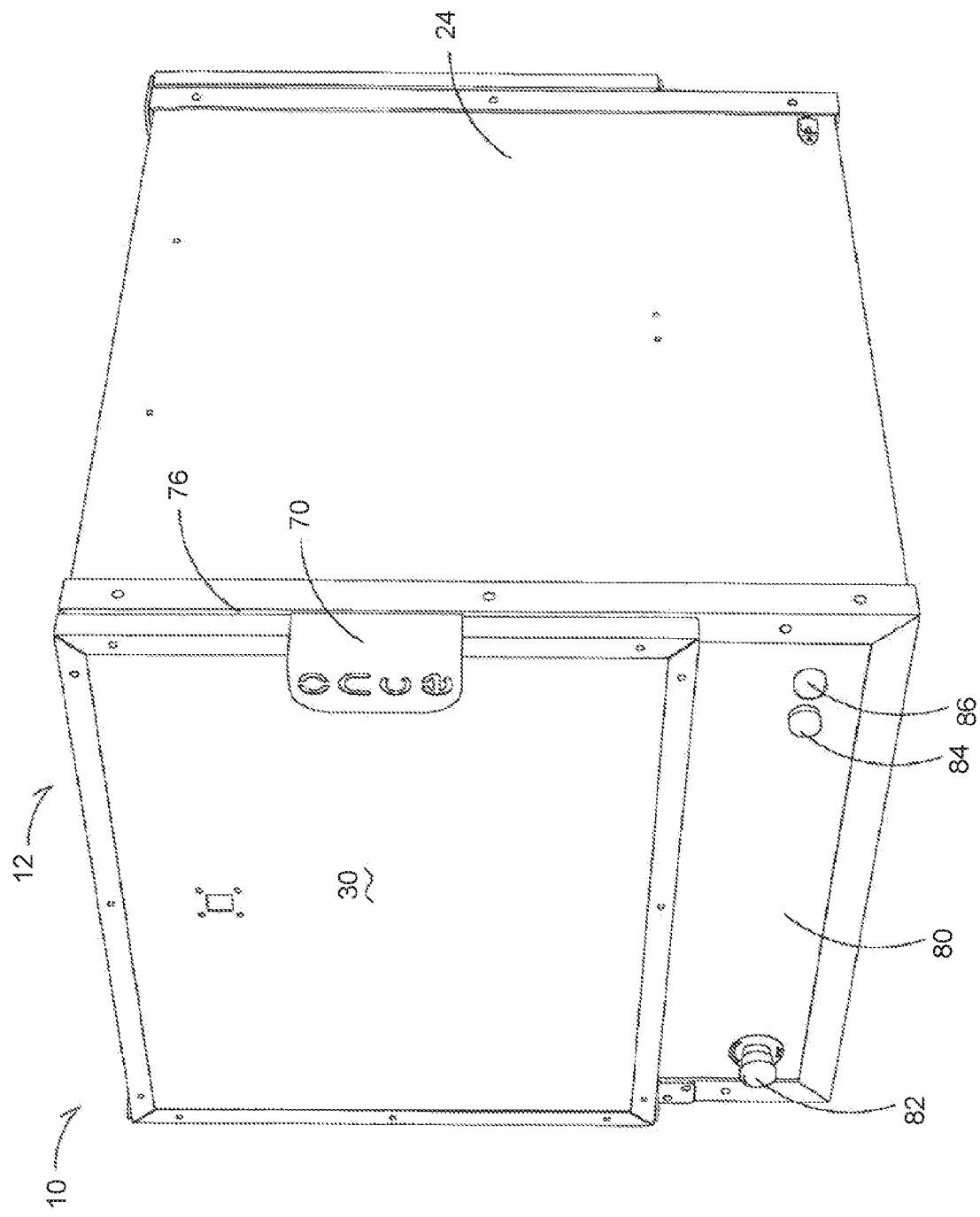
FIG. 2 is a perspective view of a sanitation chamber in a closed position.
Figure 3:
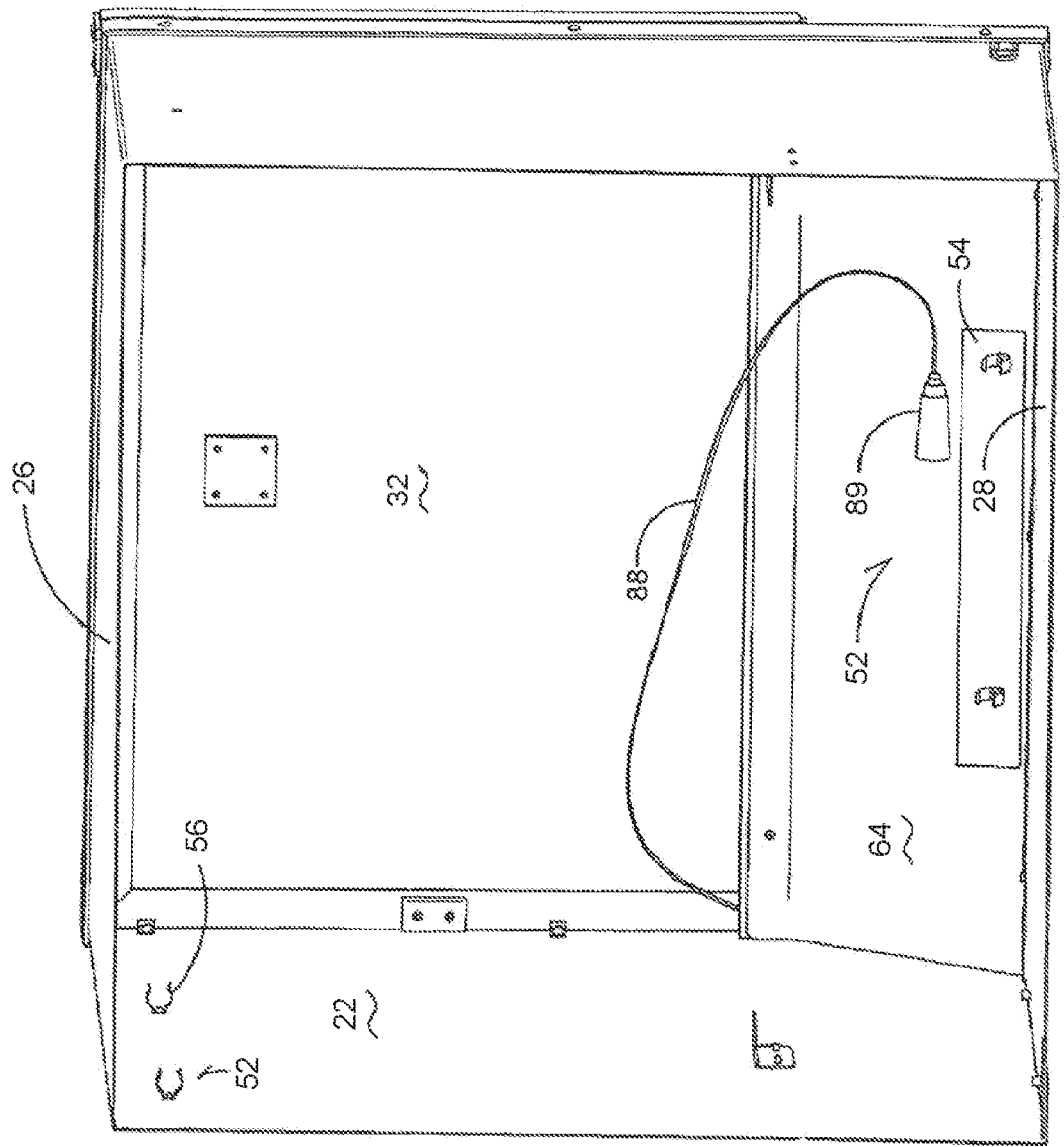
FIG. 3 is a cut away perspective view of a sanitation chamber.

FIGS. 1-3 depict a chamber 10 having a body 12 that in an embodiment is generally shaped like a box, or has a rectangular cross section. In particular, in this embodiment the body 12 has a frame 14 with first support members 16 running in parallel spaced relation in an X-axis, second support members 18 running in parallel spaced relation in a Y-axis and perpendicular to the first support members and third support members 20 running in parallel spaced relation in a Z-axis perpendicular to both first and second support members 16 and 18, thus forming the frame 14 having a square or rectangular cross section.

The first, second and third support members 16, 18 and 20 support first and second sidewalls 22 and 24 that are in parallel spaced relation that extend between a top wall 26 and bottom wall 28. First and second door members 30 and 32 are hingedly connected to the first and second sidewalls 22 and 24. The door members 30 and 32 while described as hingedly connected can be connected to the first and second sidewalls 22 and 24 in other manners that allow the door members 30 and 32 to be opened to gain access to the open interior of the chamber. This includes being connected to the top or bottom walls 26 and 28.

The interior of the chamber includes a retractable tray member 36 on which one or more items 38 such as clothing, pieces of jewelry, feed, packages, water containers, tools, beverage containers and the like can be placed. In an example, the tray member 36 is within tracks and slides outwardly until engaging a stop member. In other examples the tray member 36 is on rollers and again engages a stop member when extended. By having two separate door members 30 and 32 in association with the tray member 36 an individual can place the items 38 into the first door member 30, then go through decontamination themselves, and then get their items 38 through the opposite door member 32. This provides a user with additional flexibility and functionality regarding where to locate the UV reflective material. The reflective plate 54 surrounds attachment members 56 such as c-shaped clamps. In this example the lighting device has a transparent tubular body 58 that preferably is made of a material that absorbs a minimal amount of UV wavelength light, or a wavelength between 100 nanometers (nm) and 400 nm, more preferably 200 nm-300 nm, even more preferably between 250 nm-260 nm, and more preferably approximately 254 nm, to the interior of the chamber 10.

In this example a first light holder 52 is secured to the body 12 of the chamber 10 running along the corner of the chamber 10 created between the first sidewall 22 and the top wall 26 and extending the length of the interior 34. When in place the PCB is angled at the center of tray member 36 and the reflective plate 54 arcuately extends around the tube in approximately a half circle such that a maximum amount of light is directed directly at the tiny member 36. Similarly a second light holder 52 extends in the opposite corner of the chamber 10 adjacent the second sidewall 24 and top wall 26 again having the same light holder 52 and with the UV radiation toward the tray member 36. While these lighting devices have been described as on a light holder 52, the lighting devices could be secured directly to the chamber 10 or other similar mounting means without falling outside the scope of this disclosure. Also, while the lighting device 50 has been described as UV wavelength as described above angled toward the tray member 36. The lighting device 50 in one example has an electrical connector 63 that can only be inserted our actuated with a predetermined connector. In this manner, if an individual were to remove the chamber, they would be unable to power the lighting device 50 from a common power source or common means to ensure UV reflective material that absorbs a minimal amount of reflective materials the chamber maximizes the effect of UV radiation is maximized.

A control panel 80 is disposed below each door member 30 and 32 and includes an emergency stop button 82, a timer button 84 and an indicator light 86. Disposed within and originating from a compartment within the chamber 10 is electrical wiring 88 for the electronic components 50, 72, 82, 84 and 86 of the UV lighting devices 50 that only plug into the connector of the UV light that can be harmful to the eyes of humans cannot be emitted by the lighting devices 50 when a door member 30 or 32 is open.

Figure 4:
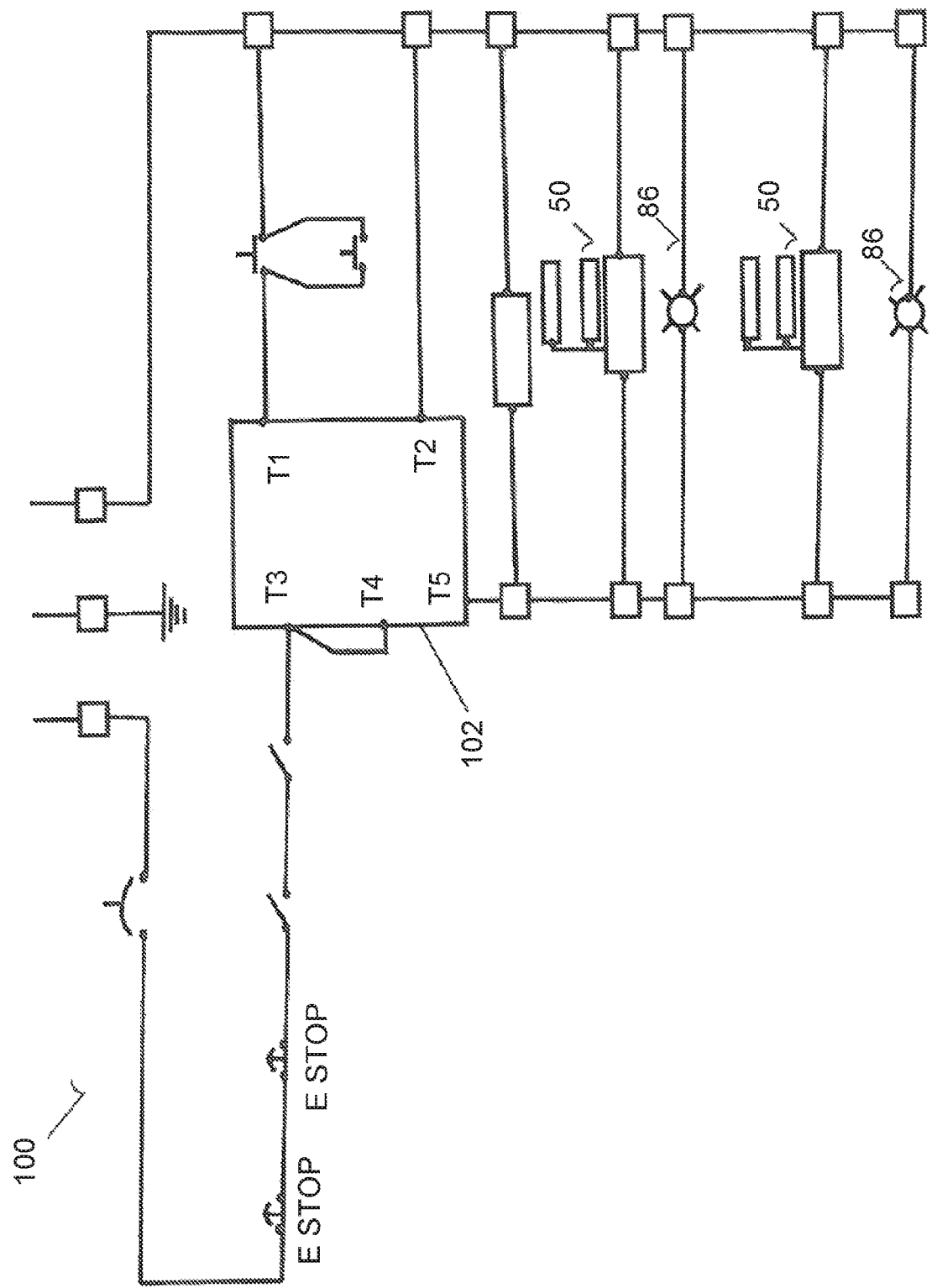
FIG. 4 is a schematic diagram of a timing circuit of a sanitation chamber.

In FIG. 4, a timing circuit 102 is connected to the input line L and neutral line N and is electrically connected to the timer button 84, such that when both door members 30 and 32 are closed and interlocked and a timer button 84 (PB1 and PB2) is actuated the timing circuit 102 is actuated. The timing circuit provides current to the ballasts (BL1 and BL2, and BAL1 and BAL2) of lighting devices 50 for a predetermined period of time. In one example the predetermined period is approximately two minutes. The predetermined amount of time can be several seconds to several days without falling outside the scope of this disclosure.

The timing circuit 102 is also connected in parallel with the ballast (BL1 and BL2, and BAL1 and BAL2) for the lighting devices 50 indicator lights 86 (LT1 and LT2) such that while the lighting devices 50 receive current the indicator lights 86 similarly receive current and lights to provide a warning to users that the chamber 10. This provides a warning to a user that the door members 30 and 32 should remain closed.

In operation, the chamber 10 is placed at the entrance of a swine facility. When an individual comes to the swine facility, before entering the individual takes any packages, feed, water, jewelry, shoes, clothing tools, or the like and takes such items 38 and places them on the tray member 36. At this time the individual closes the chamber 10, ensuring the door members 30 and 32 are magnetically interlocked. Then the individual engages a timer button 84. If both door members 30 and 32 are not interlocked the electrical system 100 will not actuate as a result of the switches SW1 and SW2 and circuit relays C1 and the lighting devices 50 do not emit chamber and be harmful to a user.

If the door members 30 and 32 are completely closed and interlocking has occurred, the switches SW1 and SW2 and circuit relays CR1 provide a completed circuit allowing current to flow to the timing circuit 102. Thus, when the timer button 84 is actuated current flows to the ballasts (BL1 and BL2, and BAL1 and BAL2) of lighting devices 50 to direct UV radiation is present and the door members 30 should remain closed. In an example, the magnetic interlocking prevents opening of the door members 30 and 32 during the predetermined period of time. If a user ignores the indicator lights 86 and is able to open a door member 30 or 32, the circuit is no longer operable as a result of the switches SW1 or SW2 and the circuit relays CR1 thus stopping current flow to the ballasts (BL1 and BL2, and BAL1 and BAL2) of lighting devices 50 and the indicator lights 86 shut off. If a malfunction occurs and current continues to flow to the ballasts (BL1 and BL2, and BAL1 and BAL2) of lighting devices 50 and the indicator lights 86 remain on, a user recognizing this can actuate an emergency stop switch (ES1 or ES2) by actuating the emergency stop button 82.

Thus multiple methods are presented to minimize and eliminate an individual from being exposed to potentially harmful UV radiation radiates the item or items 38. Thus if a germ, microorganism, virus or the like is on the item 38 it is exposed to the UV radiation is absorbed by DNA of these microorganisms breaking the molecular bonds within the micro-organismal DNA, producing thymine dimers in the DNA preventing the DNA from replicating. In this manner, cells and viruses become inactive and unable to reproduce. Thus, if a virus such as the porcine epidemic diarrhea virus is on an item 38 the exposure to the UV agricultural facility, including for chickens, turkeys, cows, horses and the like and to inactivate or kill any germ, microorganism, virus or the like, both without falling outside the scope of this disclosure. In particular, the agricultural facility.

Figure 5:
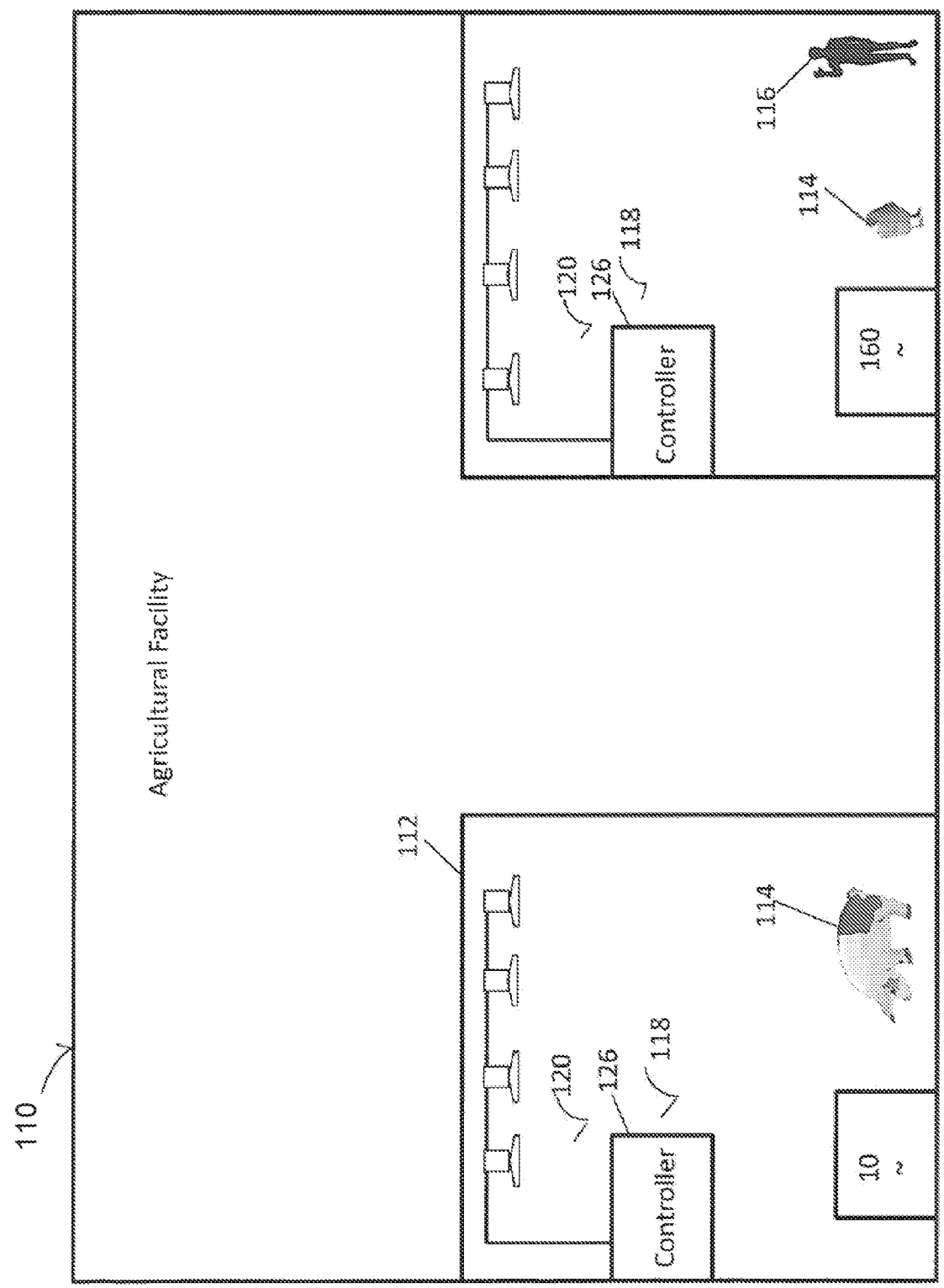
FIG. 5 is a schematic diagram of an agricultural facility.
Figure 6:
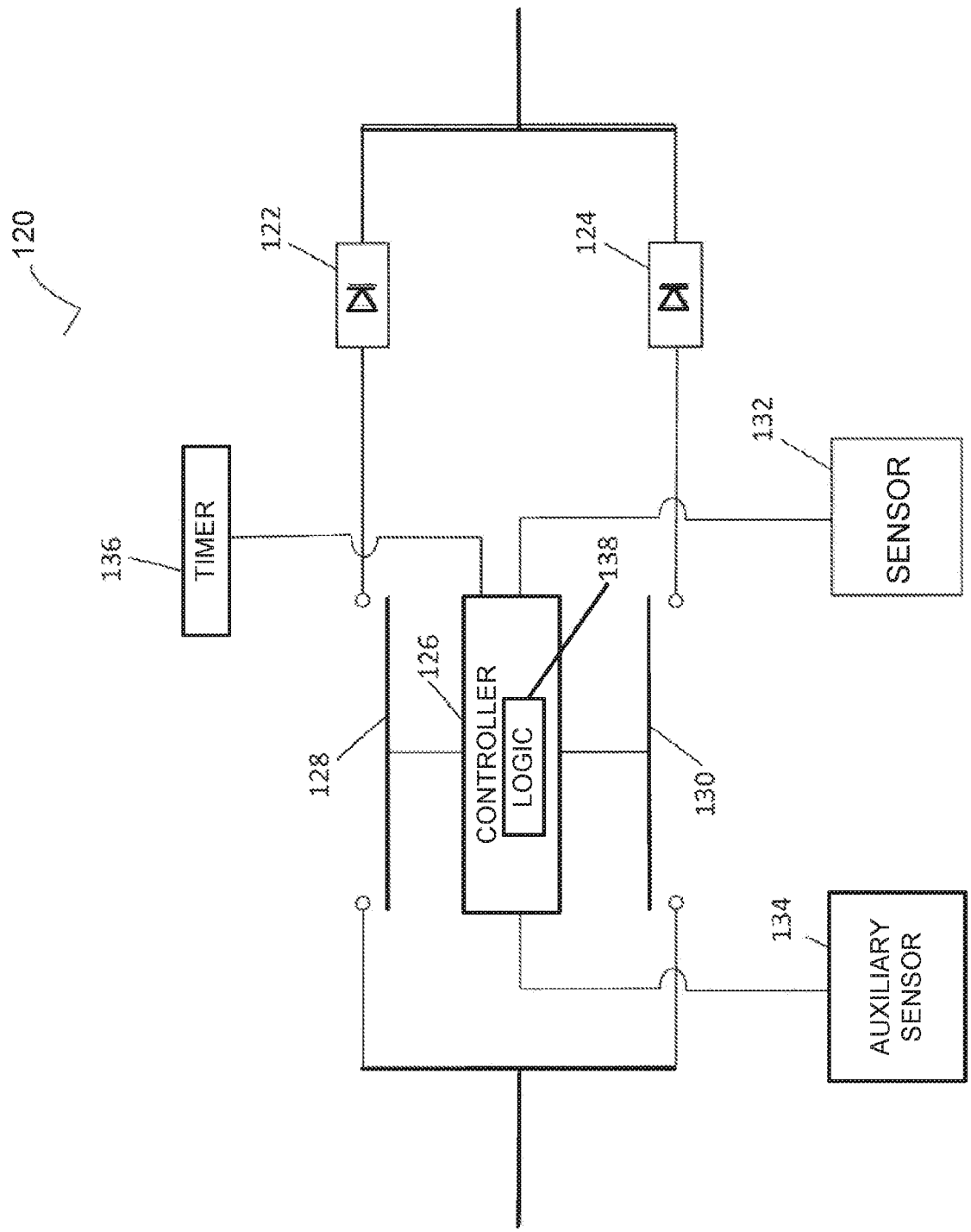
FIG. 6 is a schematic diagram of a lighting system.
Figure 7:
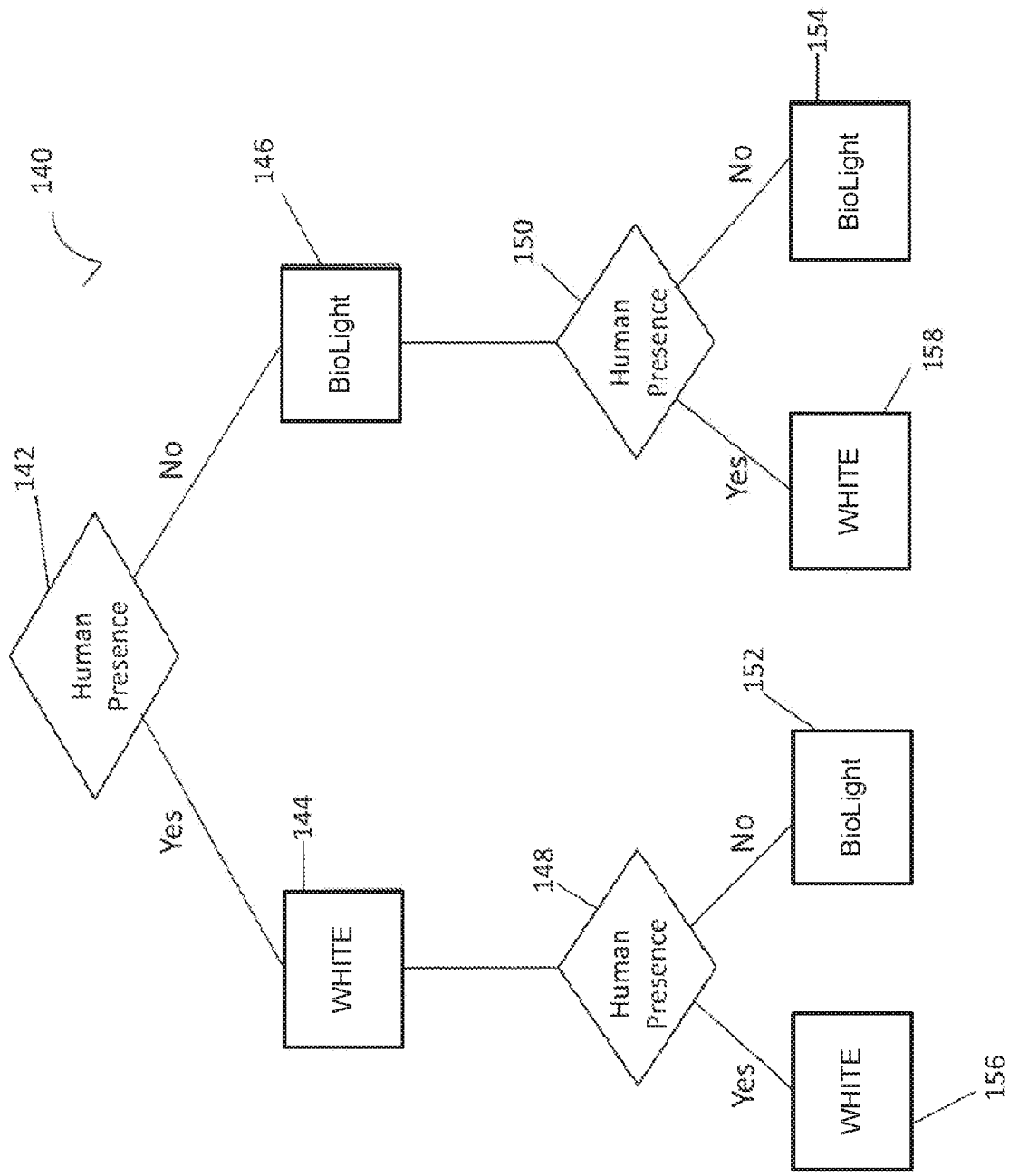
FIG. 7 is a decision flow chart of a method of sanitizing an agricultural facility.

FIGS. 5-7 show another embodiment to accomplish sanitizing an agricultural facility. The agricultural facility 110 has multiple rooms 112 for housing both livestock 114 and humans 116. Within at least one room 112 is a biosecurity system 118, The biosecurity system includes a lighting system 120 and a biosecurity chamber 10.

The lighting system 120 comprises a first lighting element that emits light at a predetermined color and a second lighting element 124 that emits light at a second predetermined color. In one example the first lighting element 122 emits white light and the second lighting element 124 emits light at a wavelength that promotes biosecurity. In one example the second lighting element 124 emits light having a narrow band of wavelength in the blue wavelength range. In one example the first and second lighting elements 122 and 124 are within a single lighting device whereas in another example the first and second lighting elements 122 and 124 are in separate lighting devices. In one example the first and second lighting elements 122 and 124 each comprise a plurality of light emitting diodes.

A controller 126 is electrically and operably connected to the first and second lighting elements 122 and 124 to operate the lighting elements 122 and 124. In one example the controller is connected to first and second lighting elements by first and second switching elements 128 and 130 respectfully, such that when the controller 126 actuates the first switching element 128 the first lighting element 122 emits light and when the second switching element 130 is actuated the second lighting element 124 emits light.

The controller 126 is also electrically connected to and receives information from sensor 132 and auxiliary sensor 134. The sensor 132 in one example is a motion detector that determines when an individual is within a predetermined space. The auxiliary sensor 134 determines an environmental condition associated with the room 112 in which the auxiliary sensor 134 is located. In an example, the environmental condition is the humidity within the room 112, and in another example the environmental condition is the temperature within the room 112. Similarly, the auxiliary sensor 134 could be designed to detect bacteria, a virus or predetermined chemical presence within the room 112 or a space where the second sensor is located.

The controller 126 is also electrically connected to and receives information from a timer 136. Specifically the controller has logic circuitry 138 therein that utilizes a decision matrix 140 based upon the inputs received from the first and second sensors 132, 134 and timer 136 to determine when to actuate first and second switching elements 128 and 130 to actuate first and second lighting elements 122 and 124.

FIG. 7 shows one example of the decision matrix 140. When the lighting system 120 is operating the first sensor 132 is operational to detect the presence of an individual at step 142. If an individual is detected, then the first switching element 128 is actuated and the first lighting element 122 is actuated such that white light is provided for the individual as indicated by step 144. If an individual is not detected, then the second lighting element 124 is actuated at a predetermined wavelength, such as blue light to inhibit bacteria growth as indicated by step 146. The first sensor 132 continues to monitor for the presence of an individual after either step 144 or 146 at steps 148 and 150. If not detected, then the second lighting element either switches to blue light at step 152 or continues to emit the blue light at step 154. If an individual is detected, then the first and second switching elements 128 and 130 are actuated accordingly and the second lighting element 124 is turned off or kept off while the first lighting element 122 remains on at step 156 or is turned on to provide white light at step 158. In an alternative example, the decision matrix may return to step 142 after entering step 144 or step 146 and a predetermined period of time has elapsed.

The decision matrix 140 can be accomplished in many different manners, including but not limited to utilizing a dimming system wherein a leading edge dimmer actuates the first switching element 128 and a falling edge dimmer controls the second switching element 130. In all, the decision matrix 140 can be adjusted to include a timing circuit and to have the first and second lighting elements 122 and 124 actuated simultaneously to provide simultaneous blue and white light in one example. In addition, the auxiliary sensor 134 can monitor humidity levels or other environmental conditions to detect an environment that is conductive for bacteria, viruses or other germs and adjusts the lighting system 120 to counteract the conditions by adding light, such as blue light into the environment. Thus the lighting system 120 can adjust to provide lighting for humans and still maximize biosecurity advantages.

To additionally sanitize the facility 110, in one example an ozone generator 160 is provided that generates or discharges ozone into a room 112. In one example, the ozone generator 160 is a corona discharge ozone generator. In another example, the ozone generator 160 is in communication with the sensors 132, 134 and/or timer 136 to only generate ozone when a human is not detected in the facility 110 or at a time humans are not allowed into the facility 110. In another example, the environmental condition detected by a sensor 132 or 134 is the level of ozone within the facility 110 or room 112 of the facility 110 and the ozone generator 160 is in communication with a security system of the facility 110 to keep doors of the facility 110 locked until a safe level of ozone for humans is within the facility.

Figure 8:
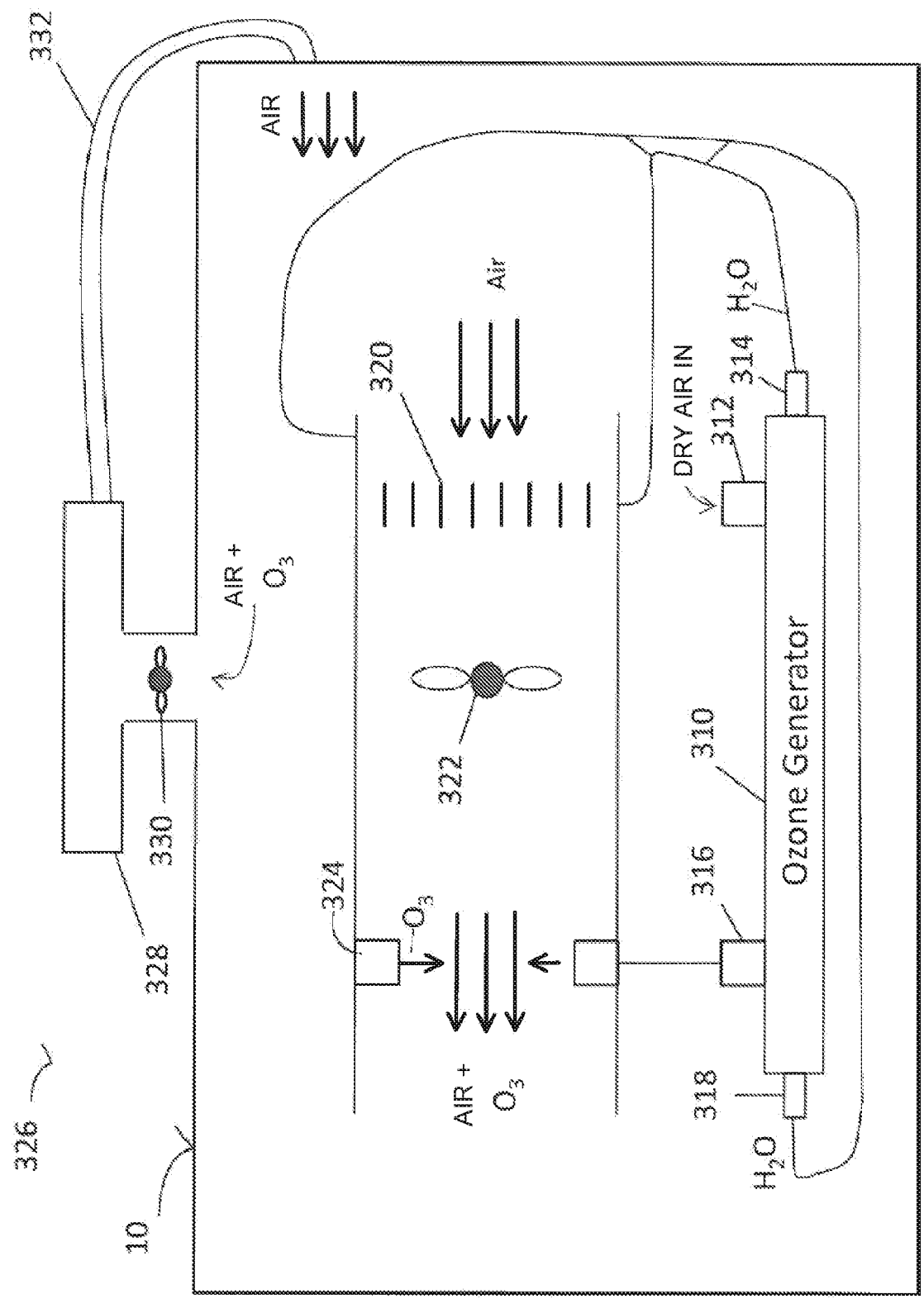
FIG. 8 is a schematic diagram of a sanitation chamber.
Figure 9:
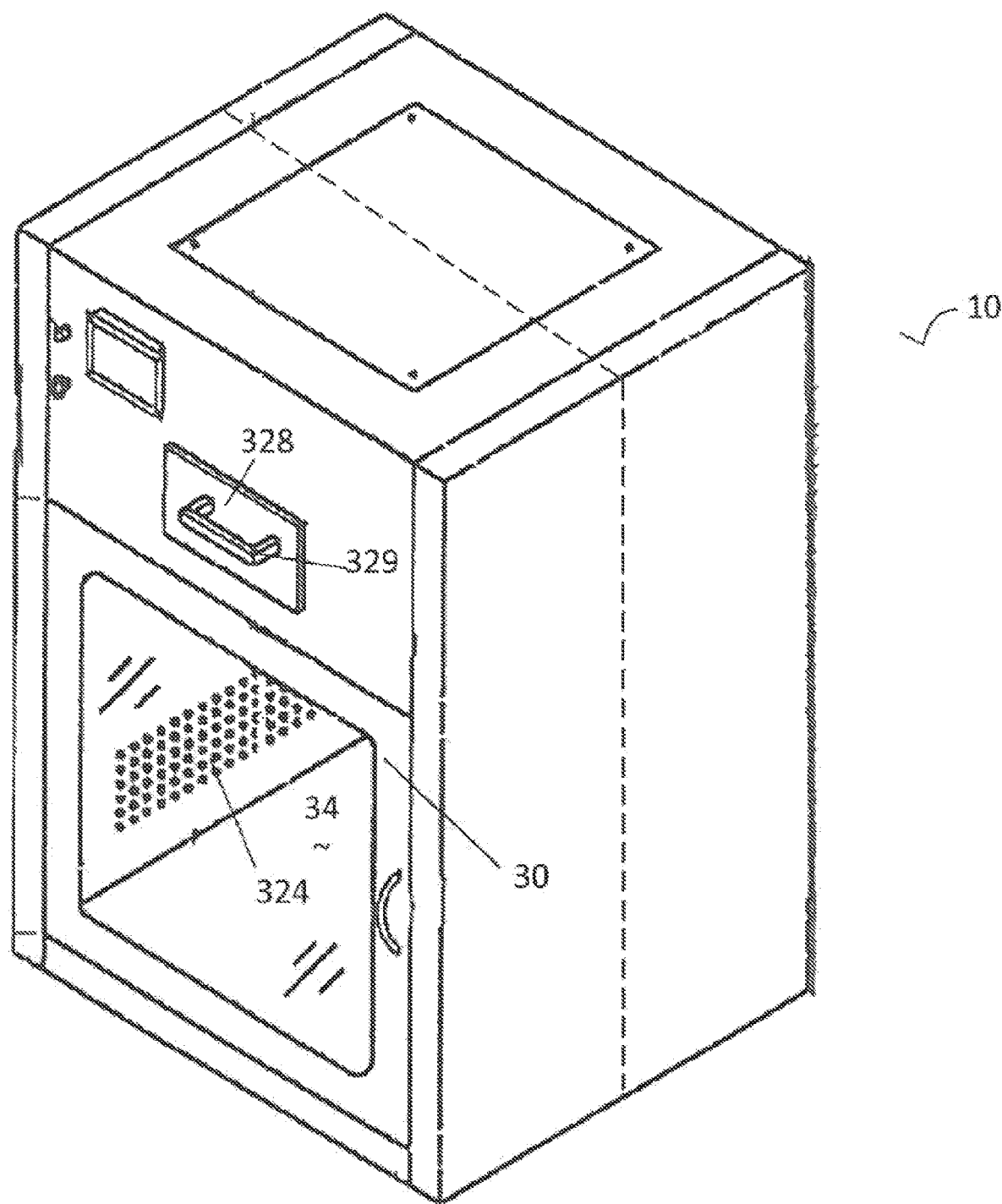
FIG. 9 is a perspective view of a sanitation chamber.
Figure 10:
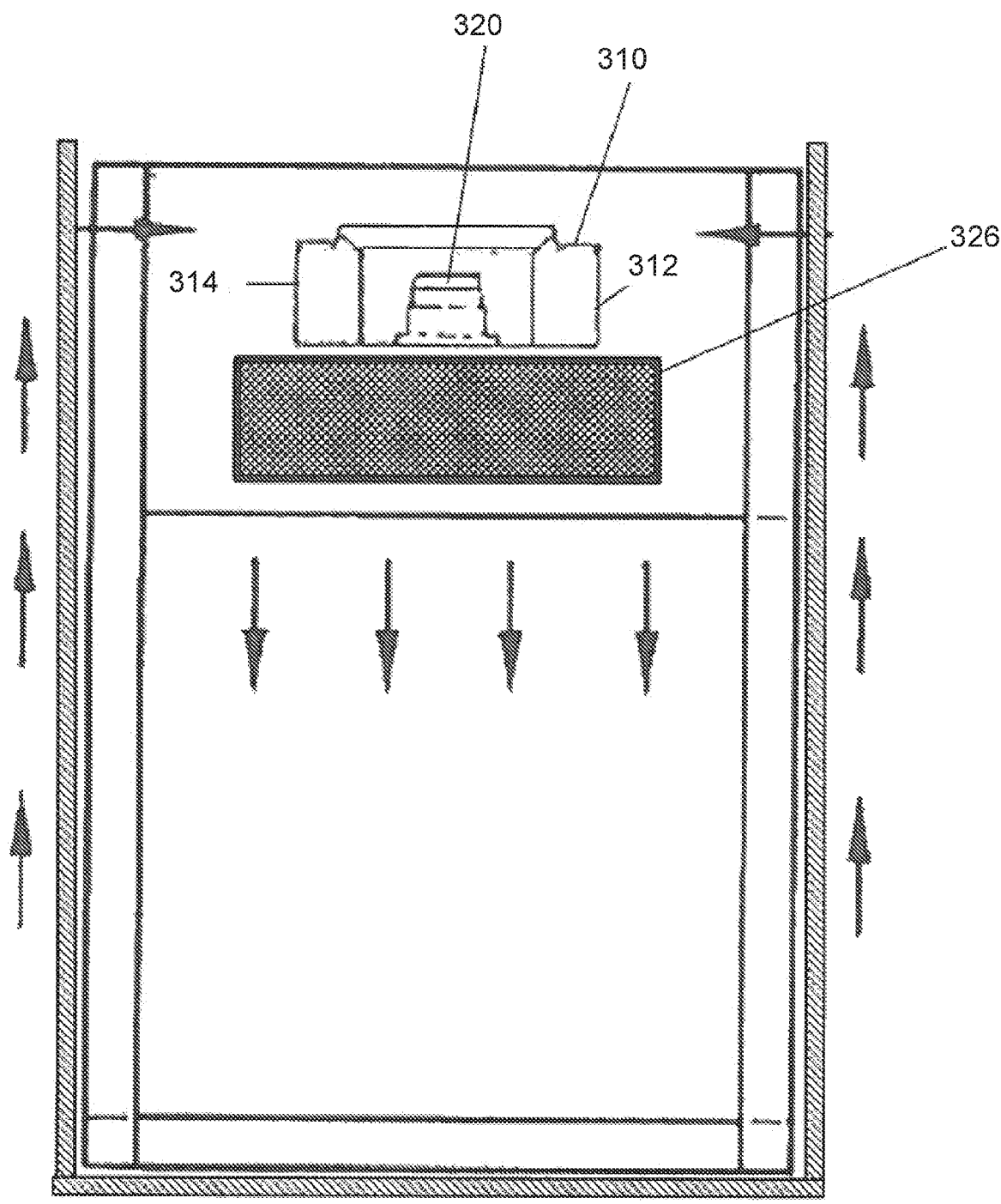
FIG. 10 is a front plan view with hidden lines of a sanitation chamber.

FIG. 8 shows another example embodiment of the chamber 10. An ozone generator 310 in one example has an air intake 312 and water intake 314 to generate O3 through ozone outlet port 316 and water outlet port 318. The water from the water outlet port 318 flows to a radiator 320 positioned adjacent a fan element 322 to move heated water vapor through an ozone discharge port 324 to discharge air and ozone into the chamber 10. The ozone generator 310 in one example generate ozone through a corona discharge. The ozone combines with either UV light or blue light to become even more effective at killing and inactivating bacteria and viruses.

An ozone filter system 326 is secured to the chamber to ensure when the chamber 10 is opened that harmful levels of ozone do not exist. The filter system 326 includes a carbon filter 328 that has an intake fan 330 and in one example utilizes active charcoal. In one example the filter 328 has a handle 329 and is removable and thus easily replaced with another filter. A conduit 332 conveys the filtered oxygen back into the interior of the chamber 10. The timing circuit of the chamber 10 is electrically connected to the ozone generator 310 to keep the door of the chamber locked for a predetermined period after shutting off the generator 310 to filter the air to have a safe level of ozone for humans before the chamber 10 can be opened.

One will appreciate that by using the chamber 10 with the ozone generator 310 and lighting system 120 that bacteria and viruses within an agricultural facility 110 are minimized to prevent the spread of disease. Consequently disease is prevented and facilities are saved from massive losses. Thus, at the very least all of the problems of the background have been overcome.

In one example a method of sanitizing an agricultural facility is provided that includes monitoring at least one room of an agricultural facility with a sensor to detect a human. A first light is provided having a first spectral content when a human is detected. A second light is provided having a second spectral content within a narrow range of wavelengths to inhibit bacteria growth when a human is not detected.

In one example, the narrow range of wavelengths is in between 410 nm-450 nm. In another example, the narrow range of wavelengths is in the blue range of wavelengths. In yet another example, the sensor is a motion detector.

In one example an additional step of monitoring the room with an auxiliary sensor and providing the second spectral content based on an environmental condition of the room detected by the auxiliary sensor is provided. In another example, the first light is provided by a light emitting diode. In yet another example, an additional step of discharging ozone into the room for a predetermined period when a human is not detected is provided. In one example, the ozone is discharged by corona discharge.

In another example, another method of sanitizing an agricultural facility is provided. A chamber having an open interior is placed within the agricultural facility. Next an item is placed within the chamber. Then the open interior is enclosed. Then light having a spectral content within a narrow range of wavelengths from at least one lighting device is directed toward the item for a predetermined amount of time to inactivate a microorganism. Then ozone is discharged into the open interior.

In one example, the open interior is enclosed by a magnetically interlocked door. In another example, and additional step of providing an ozone filter system including an intake fan that conveys ozone from the open interior to a filter that converts ozone into oxygen is provided. In another example, the filter comprises active charcoal.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. A method of sanitizing an industrial livestock facility, comprising:
monitoring at least one room of the industrial livestock facility with a sensor operably connected to a controller to detect that a human is present in the at least one room;
monitoring the at least one room with an auxiliary sensor operably connected to the controller;
providing a first light having a first spectral content when the human is present using a first lighting element;
providing a second light having a second spectral content within a narrow range of wavelengths to inhibit bacteria growth when the human is not detected using a second lighting element, wherein the controller is operably connected to the first lighting element by a first switching element and to the second lighting element by a second switching element and actuates the first and second switching elements based on the presence of the human detected by the sensor; and providing the second spectral content using the controller to actuate the second switching element based on an environmental condition of the room detected by the auxiliary sensor, wherein the environmental condition relates to humidity or a predetermined chemical.

2. The method of claim 1 wherein the narrow range of wavelengths is in between 410 nanometers and 450 nanometers.

3. The method of claim 1 wherein the narrow range of wavelengths is in between 100 nanometers and 400 nanometers.

4. The method of claim 1 wherein the narrow range of wavelengths is in a blue range of wavelengths.

5. The method of claim 1 wherein the sensor is a motion detector.

6. The method of claim 1 wherein the first light is provided by a light emitting diode.

7. The method of claim 1 further comprising discharging ozone into the at least one room for a predetermined period when the human is not detected.

8. The method of claim 7 wherein the ozone is discharged by corona discharge.

9. The method of claim 1 wherein the first spectral content and the second spectral content are different.

10. A biosecurity system for an industrial livestock facility, comprising:
   a sensor to monitoring at least one room of the industrial livestock facility and to detect a human presence in the at least one room, the sensor operably connected to a controller;
   an auxiliary sensor to monitor the at least one room, the auxiliary sensor operably connected to the controller:
   a first lighting device having a first spectral content being illuminated when the human presence is detected, the first lighting device operably connected to a first switching element;
   a second lighting device having a second spectral content within a narrow range of wavelengths being illuminated when the human presence is not detected, wherein the second spectral content inhibits growth of a bacterium, the second lighting device operably connected to a second switching element; and
   wherein the controller is operably connected to the first switching element and the second switching element and actuates the first and second switching elements based on the presence of the human detected by the sensor, further wherein the controller actuates the second switching element to enable emission of the second spectral content based on an environmental condition of the room detected by the auxiliary sensor, and further wherein the environmental condition relates to humidity or a predetermined chemical.

11. The biosecurity system of claim 10, wherein the narrow range of wavelengths is in between 410 nanometers and 450 nanometers.

12. The biosecurity system of claim 10, wherein the narrow range of wavelengths is in between 100 nanometers and 400 nanometers.

13. The biosecurity system of claim 10, wherein the narrow range of wavelengths is in a blue range of wavelengths.

14. The biosecurity system of claim 10, wherein the sensor is a motion detector.

15. The biosecurity system of claim 10, wherein the first light is provided by a light emitting diode.

16. The biosecurity system of claim 10, wherein the first spectral content and the second spectral content are different.

\* \* \* \* \*